United States Patent [19]

Shimizu et al.

[11] Patent Number: 4,709,157
[45] Date of Patent: Nov. 24, 1987

[54] METHOD AND APPARATUS FOR INSPECTING WEB SURFACE

[75] Inventors: Shigehisa Shimizu; Takao Otokozawa, both of Kanagawa, Japan

[73] Assignee: Fuji Photo Film Co., Ltd., Kanagawa, Japan

[21] Appl. No.: 765,116

[22] Filed: Aug. 13, 1985

[30] Foreign Application Priority Data

Aug. 13, 1984 [JP] Japan .................. 59-167904

[51] Int. Cl.⁴ .......................................... G01N 21/88
[52] U.S. Cl. ................................... 250/572; 356/444
[58] Field of Search ............... 250/548, 557, 571, 572, 250/223 R, 562, 563; 356/444, 237, 430, 431; 358/106

[56] References Cited

U.S. PATENT DOCUMENTS

| | | | |
|---|---|---|---|
| 4,410,278 | 10/1983 | Makihira et al. | 250/563 |
| 4,432,013 | 2/1984 | Miller et al. | 358/106 |
| 4,486,777 | 12/1984 | Yamamura | 358/106 |
| 4,507,564 | 3/1985 | Shimada | 250/563 |
| 4,549,206 | 10/1985 | Suzuki et al. | 250/563 |
| 4,553,838 | 11/1985 | Madsen | 356/237 |

*Primary Examiner*—David C. Nelms
*Attorney, Agent, or Firm*—Young & Thompson

[57] ABSTRACT

Method and apparatus for inspecting a surface having a photosensitive layer on a wide film web from which lateral margins are slit away, by detecting defects of the photosensitive layer of the surfaces of the lateral margins. The intensity of a line of light which is projected onto a lateral margin of the web is modulated by the surface of the lateral margin and received by reflection by a line sensor for producing an analog video signal which in turn is converted into two binary signals of high and low output levels. From the combination of the two binary signals, the presence of a defect is detected, because the intensity of the modulated reflected light will vary from a value characteristic of the absence of a defect.

14 Claims, 5 Drawing Figures

METHOD AND APPARATUS FOR INSPECTING WEB SURFACE

BACKGROUND OF THE INVENTION

This invention relates to web surface inspection and, more particularly, to a method and apparatus for detecting the presence and location of defects of a photosensitive layer on a film web.

In general, the production of photographic roll films includes processes of sequentially applying multiple layers of photosensitive material onto a wide web of film base, winding the film up in a roll, and then slitting and cutting it into a plurality of film strips with a desired width and length while moving it lengthwise. When the application of photosensitive material is effected while moving a wide web of film base lengthwise, it is difficult to apply a uniform layer of photosensitive material to lateral margins of the wide web. For this reason, a certain width of the lateral margins will be slit away from the wide web in said slitting process and discarded.

However, the remaining major part of the wide web from which a plurality of strip films are made sometimes also has defects in the layer of photosensitive material. These defects, in the majority of cases, occur also in the lateral margins. Therefore, it is necessary to inspect the lateral margins in order to detect such defects in the remaining major part of the wide web. For this purpose, heretofore, the lateral margins slit away from the web in the slitting process have been retained and wound up for each web roll for subsequent visual inspection in order to find defects in the layer of photosensitive material which can be regarded to have spread to the major part of the wide web and, if found, to identify their locations. By such the visual inspection, however, it is difficult to identify the corresponding exact locations on the remaining major part of the film strip which has been wound up. As a result, it is hardly avoidable to cut away excessive areas of the web or film strip including defects. Because visual inspection must be effected for each web roll, the processes following slitting will be delayed. Furthermore, there is a variation in the results of visual inspections, between different inspectors.

For the purpose of automatically effecting such web surface inspections, there is known in the art a technique by which the defects of the application of photosensitive material layer to the web of film base are found by illuminating the web surface to be inspected. Such a technique is disclosed in, for example, Japanese Utility Model Publications Nos. 45-23978 and 46-25437, and Japanese Patent Unexamined Publications Nos. 58-68651 and 58-68652. This technique is characterized by inspecting the entire width of a wide web, resulting in a reduced inspection accuracy. Particularly, when this technique is applied to the inspection of photosensitive film webs, not only is the selection of an illumination source restricted owing to the photosensitivity of the film web, but also it is difficult to produce an output signal with an increased signal-noise (SN) ratio owing to the use of a low intensity of illumination light. Furthermore, there is a great possibility that defects occurring only in the lateral margins to be slit away may be incorrectly identified as occurring in the remaining major part of film web. Such misrecognition is avoidable if the web is inspected after the lateral margins have been slit away. In this case, two processes are required; one for slitting away the lateral margins from the web, and the other for slitting and cutting the remaining major part to strip films with a desired width and length.

OBJECTS OF THE INVENTION

It is therefore an object of the present invention to provide a method and apparatus for facilitating web surface inspection with a high accuracy.

It is a further object of the present invention to provide a method and apparatus for inspecting the surface of a web without any adverse effect on the major part thereof to be used for products.

SUMMARY OF THE INVENTION

In accordance with the present invention, the foregoing objects are achieved by the provision of a method and apparatus for web surface inspection in which a line of light which is projected transversely across the entire width of the lateral margins slit away from a wide web to be used for products is modulated in intensity by the surface of the lateral margin. An analog video signal is produced in accordance with the modulated light and then converted into two binary signals of square wave of a low or high output level. A combination of the two binary signals is input to CPU for discrimination in order to detect the presence of a defect in the surface of the lateral margin and, if detected, to identify its lengthwise location thereon. The CPU provides a signal indicating the presence of a defect when any one of the binary signals is different from a specified square wave form so as to give a warning.

BRIEF DESCRIPTION OF THE DRAWINGS

The above and other objects and features of the present invention will become more apparent to those skilled in the art from the following detailed description with reference to the accompanying drawings, in which.

DETAILED DESCRIPTION OF THE INVENTION

Figure 1:
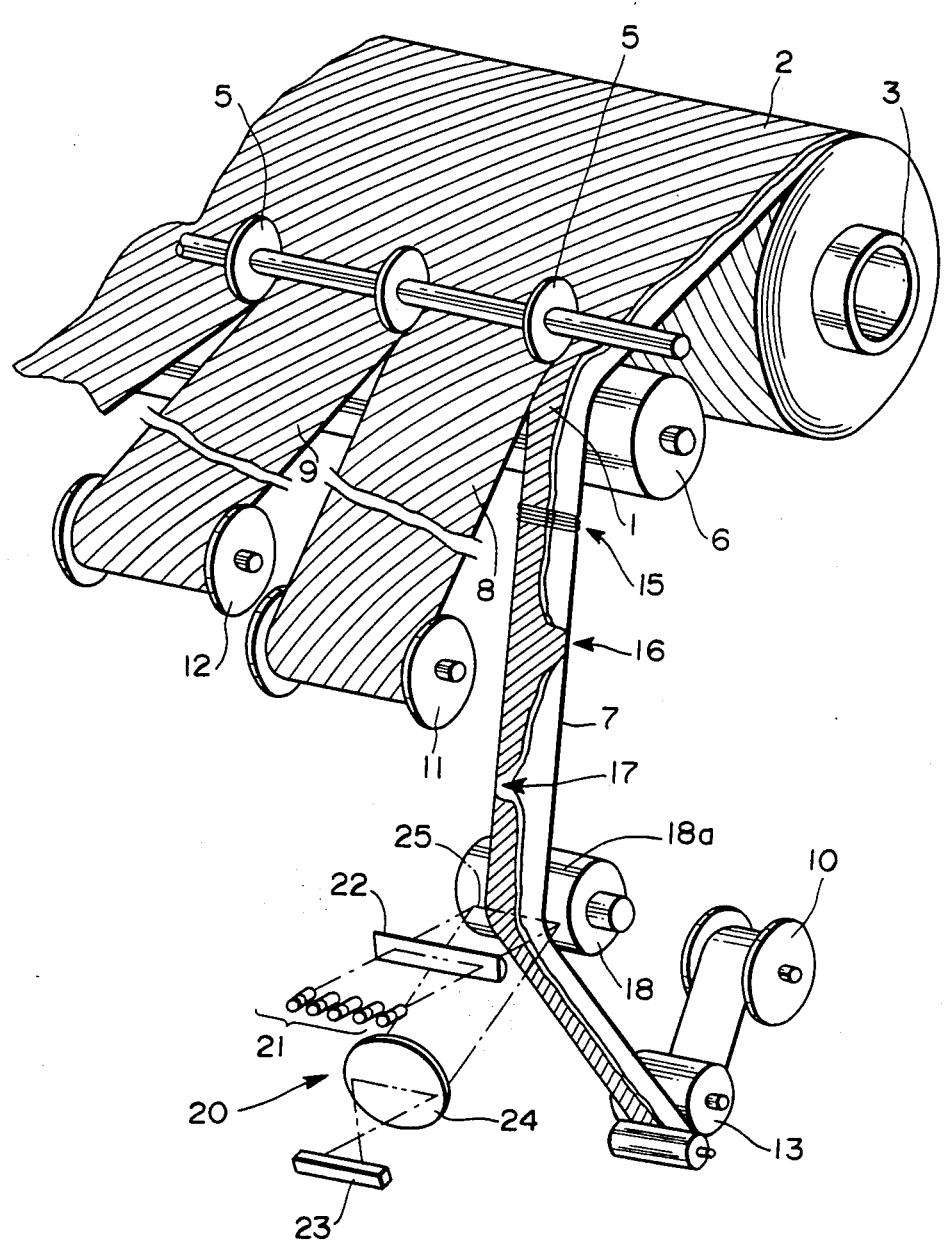
FIG. 1 is a perspective view of a surface inspection apparatus in accordance with the present invention which is applied to a film web slitting apparatus.

Referring now to FIG. 1, shown therein is a film web slitting apparatus to which a web surface inspecting apparatus according to the present invention is applied. A film web 2 with a photosensitive layer 1 is unwound from a supply core 3. The film web 2 is moved lengthwise between slitting wheels 5 and a bearing roller 6 in order not only to slit away the lateral margin 7 from the film web 2 but to slit the remaining major part into a plurality of strip films with a predetermined width, only two strip films 8 and 9 being shown for simplicity. The lateral margin 7 and strip films 8 and 9 are wound up around take-up cores 10, 11 and 12 which are driven to rotate at a uniform rate. The lateral margin 7 is wound up on the take-up core 10 through a feed roller 13.

The opposite lateral margin of the film web 2 which is, of course, slit away and wound up around another take-up core in the same way as the lateral margin 7 is omitted from FIG. 1 for simplicity.

Generally, as examples of irregularities or defects occurring on the film web 2, the following are typical: a wrinkle 15 which results from the film web 2 having been kept wound, an overextended part 16 of photosensitive layer 1 passing around behind the film web 2, and an uncoated part 17 in the photosensitive layer 1. Such defects which may spread over the major part or middle part of the film web 2 have their origins in the lateral margin. When the defects on the lateral margin 7 are found, the remaining major part of the film web 2 has to be partly slit away corresponding to the locations of the defects found on the lateral margins 7. For the purpose of finding the defects and, if found, the locations thereof, there is provided means for inspecting the lateral margin 7 slit away from the film web 2. The inspecting means includes a black roller 18 having a matte surface 18a, and an optical arrangement 20.

Figure 2:
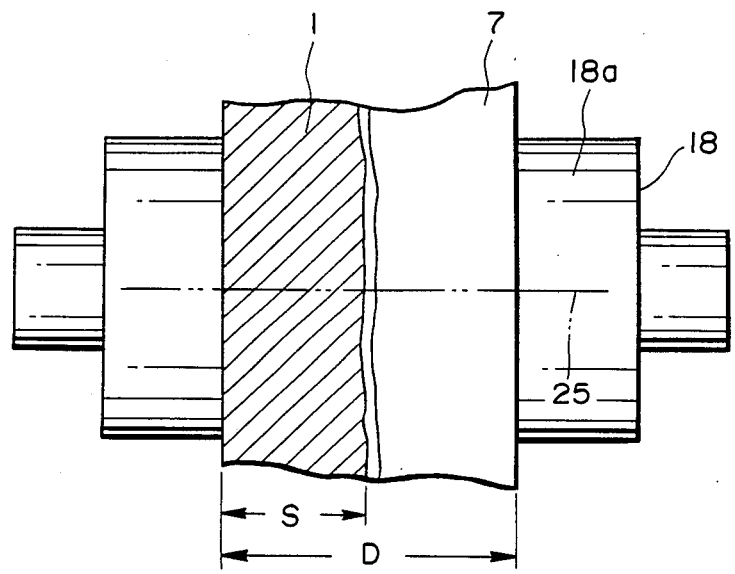
FIG. 2 is a schematic view showing a line of illumination projected onto a lateral marginal part slit off a film web.

The optical arrangement 20 comprises an illumination source 21 of a linear array of infrared light emitting diodes (LEDs), a cylindrical lens 22 for focusing light from the illumination source 21 onto the surface 18a of the roller 18 as a line of illumination, a line sensor 23 such as a charge coupled device (CCD) for receiving the reflected infrared light from the surface 18a of the roller 18, and an image forming lens 24 which is positioned to focus an image on the roller 18 onto the line sensor 23. As shown in FIG. 2, the line of light 25 is projected onto the surface 18a of the roller 18 over the width D of the lateral margin 7. The same detecting means (not shown) is provided for the opposite lateral margin.

Figure 4:
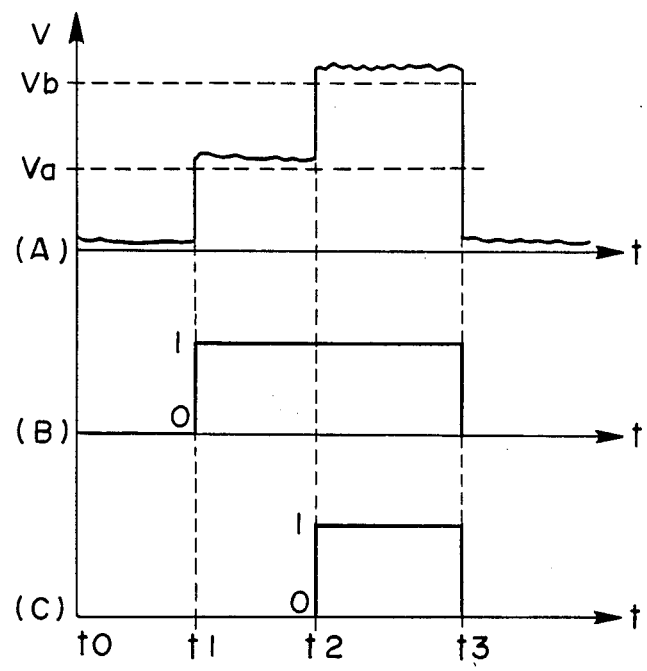
FIG. 4 shows square wave forms which are specified as desired.
Figure 3:
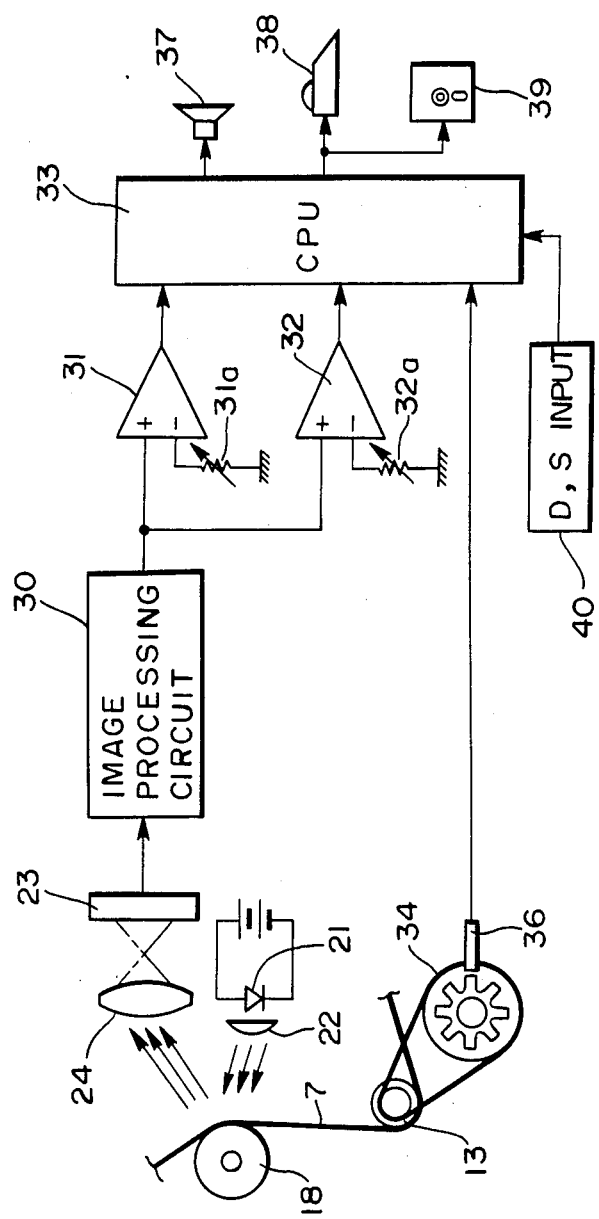
FIG. 3 is a circuit diagram of the surface inspection apparatus.

Reference is now had to FIG. 3 in which is shown in diagram form a circuit for processing the output signal of the line sensor 23. The output signal of the line sensor 23 is input to an image processing circuit 30 for the purpose of being converted into an analog video signal which is modulated in voltage. The modulation results from the reflection of the line of illumination from the lateral margin 7 bearing on the roller 18. Assuming that the lateral margin 7 is properly applied with a photosensitive layer 1 of an average width S, the output signal of the circuit 30 is an analog video signal of a wave form which is illustrated in FIG. 4, line (A), wherein the horizontal axis indicates elapsed time representing the scanning time of the line sensor 23, or the lengthwise position along the line of illumination 25. Specifically, the output voltage of the analog video signal is very low for the scanning period of time from the time $t_0$ to the time $t_1$ because the reflection of light from the surface 18a of the roller is low. For the scanning period of time from the time $t_1$ to the time $t_2$, the output voltage rises above a reference voltage Va which will be described in detail later, due to the reflection of light from the photosensitive layer 1 of the lateral margin 7. A highest output voltage above a reference voltage Vb is obtained for the scanning period of time from the time $t_2$ to the time $t_3$. The last-mentioned highest voltage is attributable to the absence of the photosensitive layer 1 of the lateral margin 7. After the time $t_3$, the output voltage drops to that for said first-mentioned scanning period of time. For the purpose of assuring discrimination of the reflected light, it is desirable to increase the SN ratio by reducing the reflection of light from the surface 18a of the roller 18.

The analog video signal thus obtained is applied to comparators 31 and 32, each being adapted to compare the input signal with its threshold value so as to provide a binary signal of square wave form of high output level (1) or low output level (0). The threshold value is set to the reference voltage Va, Vb for the comparators 31 and 32 by adjusting variable resistors 31a and 32a, respectively. Therefore, when receiving the analog video signal of the wave form illustrated in FIG. 4, line (A), the comparators 31 and 32 produce square waves of high output level (1) illustrated in FIG. 4, lines (B) and (C), respectively. Both of the square waves are input to CPU 33. To CPU 33, in addition to the binary signals of the square waves, a transported lateral margin length signal is delivered. For this purpose, there is provided means for outputting signals proportional to the transported length of the lateral margin 7. The signal outputting means includes a speed detector 36 which is adapted to detect the speed of rotation of a driving roller 34 rotatable with the feed roller (shown in FIG. 1). Alternatively, when a stepping motor is employed in this apparatus for driving either the feed roller 13 or the take-up core 10, a clock signal to be applied to the stepping motor may be delivered to CPU 33.

CPU 33 operates in accordance with the signals delivered thereto and provides a defect signal when any one of the binary signals from the comparators 31 and 32 is different from the specified wave form. Upon the occurrence of the defect signal, CPU 33 causes a buzzer 37 to sound an alarm and a printer 38 or a disk recorder to record information as to the presence of defects on a tape or a floppy disk 39.

In the operation of the web surface inspecting apparatus in accordance with the present invention, prior to commencement of the operation of the film web slitting apparatus, width information is input into CPU 33 through its port 40 in accordance with the desired width D of the lateral margin to be slit away from the film web 2 and the normal width S over which the lateral margin has been coated with the photosensitive layer 1, which are illustrated in FIG. 2. The variable resistors 31a and 32a are adjusted to set the threshold value of the reference voltage Va for the comparator 31 and Vb for the other comparator 32. Thereupon the preparation for slitting off a desired width of a lateral margin from the film web 2 is completed.

As the film web 2 is slit into film strips of a desired size, an analog video signal is obtained in real time from the web surface inspecting apparatus 20, specifically from the image processing circuit 30. The analog video signal is, after having been converted into two binary signals, compared with square waves corresponding to the desired width D of the lateral margin to be slit away and the normal width S of the photosensitive layer on the lateral margin. When the analog video signal having a wave form $F_1$ illustrated in FIG. 5, line (F) is given, the comparators 31 and 32 will produce square waves of high output level (1) illustrated in FIG. 5, lines (G), (H), which are the same square waves as shown in FIG. 4, lines (B), (C). As a result, the web surface inspecting apparatus 20 decides the lateral margin 7 slit away to have no defect.

Figure 5:
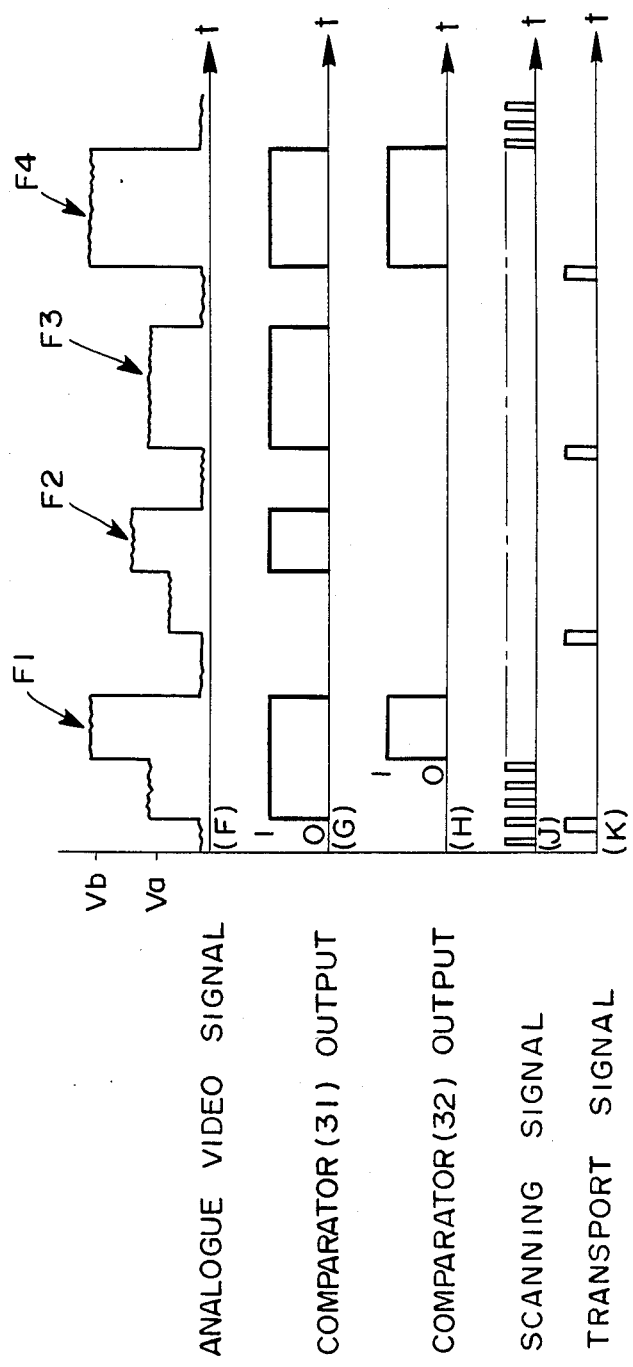
FIG. 5 is a diagram which shows various wave forms which are produced when the lateral marginal part includes defects.

Assuming that the lateral margin 7 slit away has such a defect as wrinkles 15 (shown in FIG. 1), there results diffused reflection of infrared light, and the amount of the reflected light from the wrinkles 15 of the lateral margin 7 is generally reduced resulting in the analog video signal having a wave form $F_2$ illustrated in FIG. 5, line (F). As a result, there is produced the square wave of high output level (1) illustrated in FIG. 5, line (G) from the comparator 31 and no square wave from the comparator 32. When the analog video signal having a wave form $F_3$ illustrated in FIG. 5, line (F), is emitted, only the square wave of high output level (1) is produced by the comparator 31. This means that the lateral margin 7 has an extended part 16 of photosensitive material layer 1. The same square waves produced by the comparators 31 and 32 result from the wave form $F_4$ of the analog video signal illustrated in FIG. 5, line (F). Such a combination of the same square waves represents a defect such as the uncoated part 17 of photosensitive layer 1 on the lateral margin 7.

For the purpose of finding the crosswise locations where defects have occurred on the lateral margin 7, a clock signal illustrated in FIG. 5, line (J), which in turn serves as a scanning signal for the line sensor 23 is used. In addition, pulse signals illustrated in FIG. 5, line (K), from the speed detector 36 are applied to CPU 33 for identifying lengthwise locations where defects have been detected on the lateral margin 7. The number of the pulse signals is proportional to the transported length of both of the lateral margin 7 and the film web 2.

When any one of the defects is detected. CPU 33 outputs location information in accordance with the pulse signals representing the transported length of the lateral margin 7 of the film web 2. The location information is then recorded by the printer 38 or the floppy disk 39. As will be apparent from the description relating to FIG. 5, the combinations of output signals from the comparators 31 and 32 are different from each other in accordance with the types of defects. In accordance with the location information retrieved from the CPU 33, a slitting machine separately provided is controlled to slit away the part of the film web including a defect.

The invention has been described in detail with particular reference to a preferred embodiment thereof, but it will be understood that variations and modifications can be effected within the spirit and scope of the invention. For example, light sources such as fluorescent or tungsten lamps can be used in combination with a filter having an infrared light transmitting characteristic. A line illumination light can be produced by using a rotating polygonal mirror. In this case, a photomultiplier may be used in place of the line sensor. For this reason, a driving signal for the polygonal mirror is used in order to find the crosswise location of a defect on the lateral marginal part. Furthermore, rather than an infrared illumination light a visual illumination light could be applied to inspection by leading the lateral marginal part slit away to a place where the visual illumination light is shaded from the major part of film web.

The invention can be equally applied to a web surface inspection apparatus in which the line sensor is so arranged as to receive the line of illumination passing through the lateral margin and reflected to a very limited extend by the bearing roller.

Although the above description has been given assuming the provision of a pair of surface inspection devices for the both lateral marginal parts to be slit away from a film web, it is possible to omit one of the surface inspection devices when one lateral marginal part may be widely slit off. Furthermore, as will be apparent to those skilled in the art, the present invention is applicable to a sheet film cutting apparatus with the same results.

What is claimed is:

1. A method for inspecting a photosensitive layer on a web whose lateral margins are slit away as said web is moved lengthwise, comprising:
   projecting a line of illumination across the width of at least one of said lateral margins being slit away from said web, the intensity of said illumination being modulated by contact with said at least one lateral margin to an extent that varies with the presence or absence of a defect on the illuminated margin;
   producing an analog video signal in accordance with the modulated intensity of said illumination;
   converting said analog video signal into two binary signals of square wave form of high and low output levels;
   discriminating a combination of said two binary signals for detecting the presence of a defect on said at least one lateral margin; and
   producing a defect signal when the presence of a defect is thus detected.

2. A method as defined in claim 1, further comprising producing a location signal representing the length of said web that has been moved, for identifying the lengthwise location of a thus-detected defect on said at least one lateral margin, said defect signal consisting of said location signals.

3. A method as defined in claim 2, wherein said defect signal is recorded on a recording medium.

4. A method as defined in claim 2, and producing an alarm responsive to said defect signal.

5. A method as defined in claim 2, wherein said web is a photosensitive film with a photosensitive layer applied to the middle thereof and overlying only a portion of each of said lateral margins.

6. A method as defined in claim 5, wherein said line illumination is infrared light.

7. A method as defined in claim 6, wherein said modulation results from reflection from said surface of said at least one lateral margin.

8. An apparatus for inspecting the surface of a web whose lateral margins are slit away as said web is moved lengthwise, in which said web surface inspection is effected by detecting defects on the surface of at least one of said lateral margins being slit away, said apparatus comprising:
   means for moving said at least one slit-away lateral margin with constant tension independently from the rest of said web;
   means for projecting a line of illumination across the width of said at least one slit-away lateral margin, the intensity of said illumination being modulated by contact with said at least one slit-away lateral margin to an extent that varies with the presence or absence of a defect on the illuminated margin;
   means to produce an analog video signal in accordance with the modulated intensity of said illumination;
   means for converting said analog video signal into two binary signals of high and low output levels; and
   means for discriminating a combination of said two binary signals for detecting the presence of a defect on said at least one slit-away lateral margin and for producing a defect signal based on said lengthwise location signal when said presence of a defect is detected.

9. An apparatus as defined in claim 8, and means for producing a lengthwise location signal representing the length of said web that has been moved.

10. An apparatus as defined in claim 8, wherein said discriminating means is a CPU.

11. An apparatus as defined in claim 10, further comprising means for inputting into said CPU information as to the width of said at least one slit-away lateral margin and the desired width of a photosensitive layer on said at least one slit-away lateral margin.

12. An apparatus as defined in claim 8, wherein said signal converting means comprises a pair of comparator circuits which are adapted to set threshold values of said levels to different reference voltages.

13. An apparatus as defined in claim 8, in which said means to produce an analog video signal comprises means for receiving light by reflection from the surface of said at least one slit-away lateral margin.

14. An apparatus as defined in claim 13, wherein said light receiving means comprises a line sensor and an image processing means.

* * * * *